United States Patent [19]

Rasmussen

[11] Patent Number: 4,865,566
[45] Date of Patent: Sep. 12, 1989

[54] FIXTURE FOR USE IN ESTABLISHING ELECTRICAL CONNECTION WITH A DISPOSABLE SKIN ELECTRODE

[75] Inventor: Jan Rasmussen, Olystykke, Denmark

[73] Assignee: Medicotest Systemer A/S, Olstykke, Denmark

[21] Appl. No.: 193,163

[22] Filed: May 6, 1988

Related U.S. Application Data

[63] Continuation of Ser. No. 897,531, filed as PCT DK85/00123 on Dec. 18, 1985, published as WO86/03665 on Jul. 3, 1986, abandoned.

[30] Foreign Application Priority Data

Dec. 19, 1984 [DK] Denmark .............................. 6115/84

[51] Int. Cl.⁴ .......................................... H01R 11/22
[52] U.S. Cl. .................................. 439/825; 128/639
[58] Field of Search ............................ 128/639–641; 439/816, 825–827, 830–833, 842, 848, 855

[56] References Cited

U.S. PATENT DOCUMENTS

| | | | |
|---|---|---|---|
| 2,221,651 | 11/1940 | Pelz | 339/252 R |
| 3,092,430 | 6/1963 | Miller | 339/252 R |
| 3,581,736 | 6/1971 | Zenkich | 128/641 |

FOREIGN PATENT DOCUMENTS 2387022  12/1978  France .............................. 128/640

*Primary Examiner*—Max Hindenburg
*Assistant Examiner*—Randy Citrin
*Attorney, Agent, or Firm*—Lewis H. Eslinger; Jay H. Maioli

[57] ABSTRACT

A fixture for use in establishing electrical contact between a banana plug mounted on a cable and a snap fastener on a disposable skin electrode comprises a bottom flange provided with a sleeve adapted to receive the banana plug. A resiliently expandable through hole formed at the bottom of the fixture makes it possible to snap the fixture over the snap fastener of the skin electrode, with the through hole being of length so that the snap fastener will protrude into the passage and establish electrical contact with a banana plug inserted therein.

5 Claims, 1 Drawing Sheet

FIXTURE FOR USE IN ESTABLISHING ELECTRICAL CONNECTION WITH A DISPOSABLE SKIN ELECTRODE

This is a continuation of application Ser. No. 06/897,531, filed as PCT DK85/00123 on Dec. 18, 1985, published as WO86/03665 on Jul. 3, 1986, now abandoned.

BACKGROUND OF THE INVENTION

Electromedical disposable electrodes or skin electrodes are used in particular in connection with registration of heart functions by recording of an electrocardiogram. The EKG electrode is connected with the measuring cable, usually called patient cable, of the recording apparatus.

The EKG electrode is used most frequently in connection with monitoring of patients for extended periods of time. In the development of patient cables for this purpose, good patient comfort has therefore been an essential goal. Some of the results of this are that patient cables with snap fastener connection can today be considered standard, and that the development in the manufacturing of disposable electrodes has been focussed on electrodes with snap fastener connection.

However, there is a growing demand for using EKG disposable electrodes in connection with diagnosis of heart diseases. Since the cables and non-disposable electrodes traditionally used to this end are provided with banana plugs and banana bushings, the disposable electrode for diagnosis must either be provided with a contact means which is more expensive than the ordinary ones because of the manufacturing process, or the patient cable must be supplemented with an intermediate wire between the contact means of the electrode and the banana plug of the patient cable. Such intermediate wires, however, have been found to increase the risk of electrical errors and cause inconvenience to the EKG staff.

SUMMARY OF THE INVENTION

The invention concerns a fixture for use in establishing electrical connection between banana plug mounted on a cable and a snap fastener on a disposable skin electrode; and the object of the invention is to provide such a fixture which is inexpensive to produce and enables establishment of reliable and safe electrical contact between a banana plug and a disposable electrode with a snap fastener, without the use of intermediate wires.

This object is achieved in that the fixture has a resiliently expandable opening to receive the snap fastener and a passage substantially perpendicular to the axis of said opening to receive the banana plug, said opening being of such extent in the axial direction that the snap fastener with applied fixture protrudes into the passage. Such a fixture can be applied directly to the snap fastener of the disposable electrode in such a manner that the fixture will be in good electrical contact with a banana plug inserted in the fixture.

A particularly simple and inexpensive embodiment of the fixture is stated in claim 2, and expedient details of this structure are defined in claims 3 and 4.

BRIEF DESCRIPTION OF THE DRAWINGS

The invention will be explained more fully below with reference to the drawing, in which.

DETAILED DESCRIPTION OF THE PREFERRED EMBODIMENT

Figure 1:
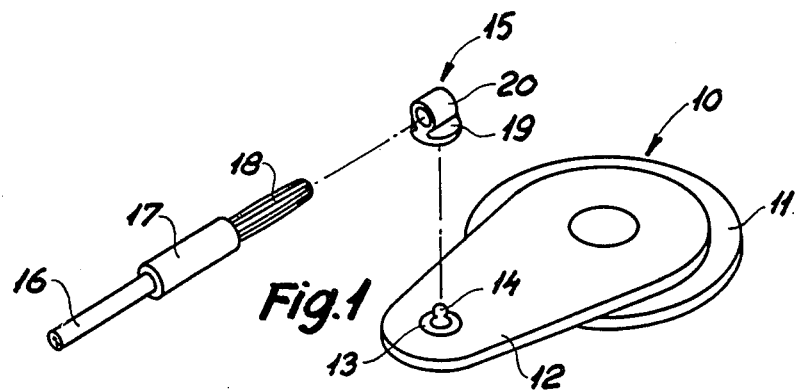
FIG. 1 is a perspective view of an embodiment of the fixture of the invention in juxtaposition with a disposable electrode, as well as with a banana plug mounted on a cable for insertion into the fixture.

In the drawing, the numeral 10 designates a disposable electrode of a generally known type, which has a circular disc 11 of foam plastic with a central hole (not shown) to receive a paste-like electrolyte. A strip-shaped metal electrode (not shown) extends over said hole and emerges at one side between two plastic cover sheets forming in combination a lateral projection 12. The outer end of this projection securely mounts a snap contact means of metal with a circular flange 13 and a contact pin 14 formed with a head.

A fixture, generally designated by 15, can be snapped onto this snap contact means. A banana plug 17 with resilient plug segments 18 mounted on a cable 16 can be inserted into the fixture.

Figure 2:
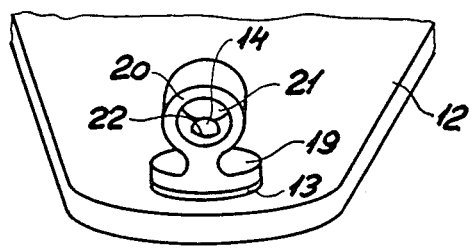
FIG. 2 is a perspective view, on an enlarged scale, of the fixture applied to the snap fastener of the disposable electrode.

As shown more clearly in FIG. 2, the fixture 15, molded of a suitably elastic plastic material, has a circular bottom flange 19 and on top of this a sleeve-shaped part 20 defining a through passage 21 to receive the banana plug. The bottom flange 19 is formed with a central hole 22 so dimensioned that the flange can be snapped down on the contact pin 14 of the disposable electrode so that the flange 19 engages the flange 13 of the snap fastener. In this applied position, shown in FIG. 2, the contact pin extends through the hole and protrudes a small distance into the passage 21 so that it is in good electrical contact with a plug segment 18 on a banana plug 17 inserted into this passage. The fixture can rotate about the pin 14 so that the cable 16 can be placed in the most convenient position for the patient.

The fixture of the invention may be arranged in other ways than the one shown in the drawing and described in the foregoing. It may e.g. be made of metal and be in the form of a base member corresponding to the flange 19, with a hairpin spring placed over its central hole and with a bushing or a spring clip secured to its top side to receive the banana plug. The sleeve 20 does not have to be closed in the plastic embodiment of the fixture either, but may be replaced by two curved, elastic walls forming an upwardly open passage. Also the flange 19 may have other shapes than the one shown.

I claim:
1. A fixture for use in establishing electrical connection between a banana plug mounted on a cable and a metal snap fastener on a disposable skin electrode, characterized in that said fixture comprises a body consisting essentially of elastic plastic material having formed therein a resiliently expandable opening means for receiving a metal snap fastener and a passage means formed in said body substantially perpendicular to the axis of and in communication with said opening means and being open at both ends for receiving a banana plug, said opening means being of such extent in the axial direction and located relative to said passage means that a metal snap fastener when applied to said fixture extends through said opening means and protrudes into the passage means and is in direct electrical contact with a banana plug when a banana plug is inserted into either end of the passage means and wherein said fixture can rotate about the metal snap fastener when the metal snap fastener is received in said opening means.

2. A fixture according to claim 1, characterized in that said body is in the form of a sleeve having a substantially planar flange in which the opening means for receiving the snap fastener is provided.

3. A fixture according to claim 2, characterized in that the substantially planar flange is formed with flange parts extending outwardly from adjoining side walls of the sleeve.

4. A fixture according to claim 1, characterized in that the opening means for receiving a metal snap fastener is located relative to the passage means for receiving the banana plug so that the metal snap fastener when so received is in direction electrical contact with a side of the banana plug at a point adjacent a base of the the banana plug when the banana plug is received in the passage means.

5. A fixture according to claim 1 characterized in that the axial length of the passage means is less than a length of resilient plug segments of the banana plug so that the tip of the banana plug protrudes beyond the passage means when the banana plug is received in the passage means.

* * * * *